United States Patent [19]

Citrin

[11] 4,058,146
[45] Nov. 15, 1977

[54] METHOD AND APPARATUS FOR TRANSFERRING LIQUID

[75] Inventor: Paul Stuart Citrin, Danbury, Conn.

[73] Assignee: Dynatech Laboratories Incorporated, Alexandria, Va.

[21] Appl. No.: 595,005

[22] Filed: July 11, 1975

[51] Int. Cl.$^2$ .............................................. B65B 3/04
[52] U.S. Cl. ..................................... 141/1; 141/238; 23/253 R; 23/259; 251/7
[58] Field of Search ............................ 141/237, 238, 1; 23/253, 259; 251/4–7

[56] References Cited

U.S. PATENT DOCUMENTS

| | | | |
|---|---|---|---|
| 2,985,192 | 5/1961 | Taylor et al. | 251/7 |
| 3,075,551 | 1/1963 | Smith et al. | 251/7 |
| 3,536,449 | 10/1970 | Astle | 141/237 |

OTHER PUBLICATIONS

IBM Technical Disclosure Bulletin, vol. 10, No. 4, Sept. 1967, pp. 399 & 400.

Primary Examiner—Houston S. Bell, Jr.
Attorney, Agent, or Firm—Strauch, Nolan, Neale, Nies & Kurz

[57] ABSTRACT

A system for accurately transferring similar small amounts of liquid from a multiplicity of containers to a corresponding multiplicity of wells in a microtitration test plate includes a multiplicity of conduits leading from a pressure chamber enclosing the containers and to which conduits the containers are individually automatically connected when the containers are loaded into the system, the conduits leading to a pinch type dispensing valve disposed above the test tray.

23 Claims, 12 Drawing Figures

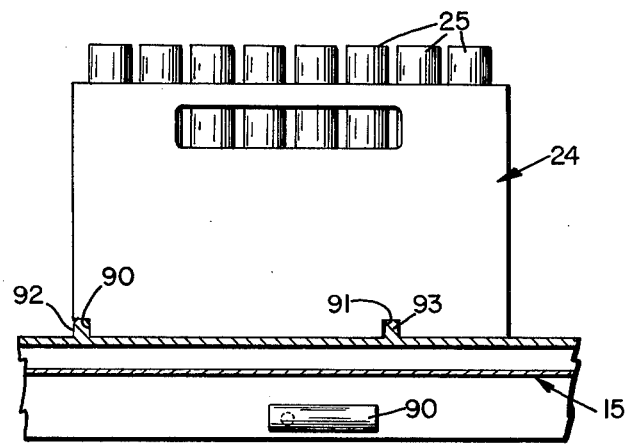
FIG. 7
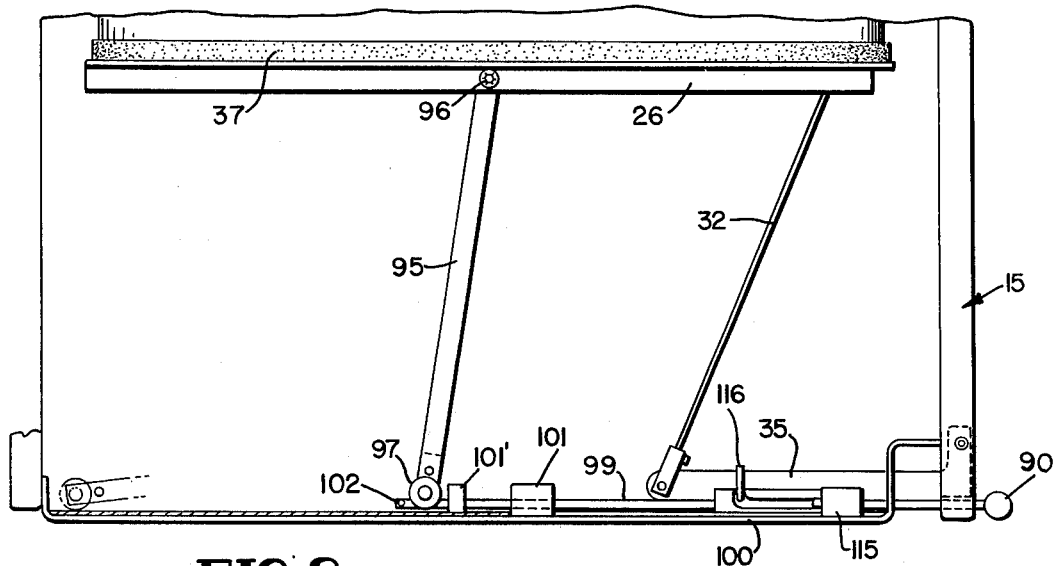
FIG. 8
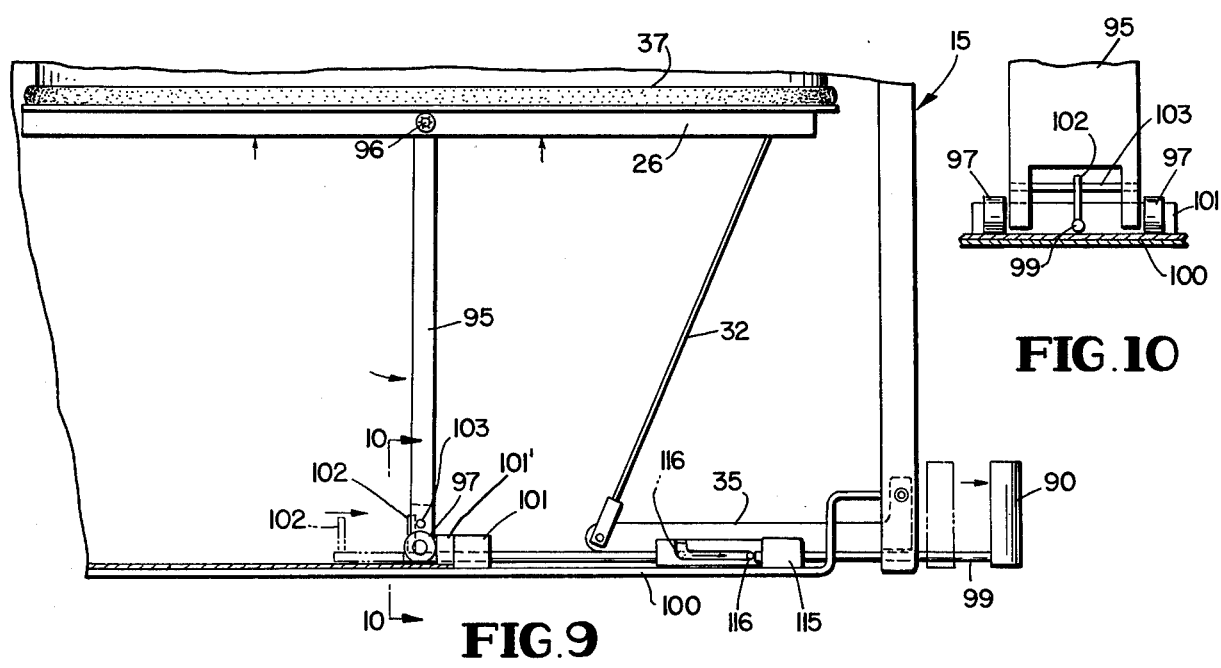
FIG. 9
FIG. 10

METHOD AND APPARATUS FOR TRANSFERRING LIQUID

METHOD AND APPARATUS FOR TRANSFERRING LIQUID

This invention relates to a system for accurately transferring in a single operation predetermined amounts of liquid from a multiplicity of containers to a corresponding number of respectively identified receptacles, and is particularly concerned with special methods and apparatus and modes of operation for carrying out the transfer in an efficient speedy manner.

The invention in a preferred embodiment has particular application in solving problems in antibiotic susceptibility testing wherein it is required that accurately metered similar amounts of a multiplicity of different liquids be transferred at the same time to identified individual wells or cells of a microtitration test tray or the like, but it is not limited to this usage.

In carrying out the invention liquids to be tested are provided in quantity in individual supply containers such as test tubes carried on a special rack which is indexed in the system so that each test tube occupies a location on the rack corresponding to the location of wells of a receiver microtitration test tray or the like that is mounted in a remote position in the system. In this embodiment the system is supported within a housing having a loading door through which the rack is so inserted that the containers are connected into a conduit arrangement leading to a special dispensing valve at which the test tray or the like is located.

The major objection of the invention is therefore to provide a novel method and apparatus wherein liquids are contained in quantity in a multiplicity of prelocated containers, such as test tubes, and in successive cycles predetermined amounts of liquid may be extracted from each of the containers and transferred through a novel conduit and valving arrangement and deposited in a correspondingly located multiplicity of cells in a microtitration plate or the like.

Further objects of the invention are to provide novel apparatus and modes of operation for carrying out the foregoing including particularly special arrangements whereby the rack of containers is automatically connected into the conduit system when the loading door is closed and a special pinch-type valve arrangement at the discharge end of the system, together with special controls and safety devices, and these will be set forth in the claims herein.

Further objects will appear in connection with the appended claims and the annexed drawings.

BRIEF DESCRIPTION OF DRAWINGS

FIG. 3 is an enlarged fragmentary view mainly in section showing the association of the pressure chamber with the dispensing valve;

FIG. 3A is a further enlarged fragmentary view in section showing valve detail and mode of operation;

FIG. 7 is a fragmentary end view showing how the container rack is keyed on the door to ensure correct orientation of the containers within the housing;

FIG. 8 is a fragmentary side elevation showing the link for effecting final upward movement of the platform to sealing condition, in the position it occupies when the loading door is closed;

FIG. 9 is a view similar to FIG. 8 but showing the link erected to force the platform into sealing position;

FIG. 10 is a fragmentary detail showing the lower end of the toggle link and the coacting pin on the end of the handle rod.

PREFERRED EMBODIMENTS

Figure 1:
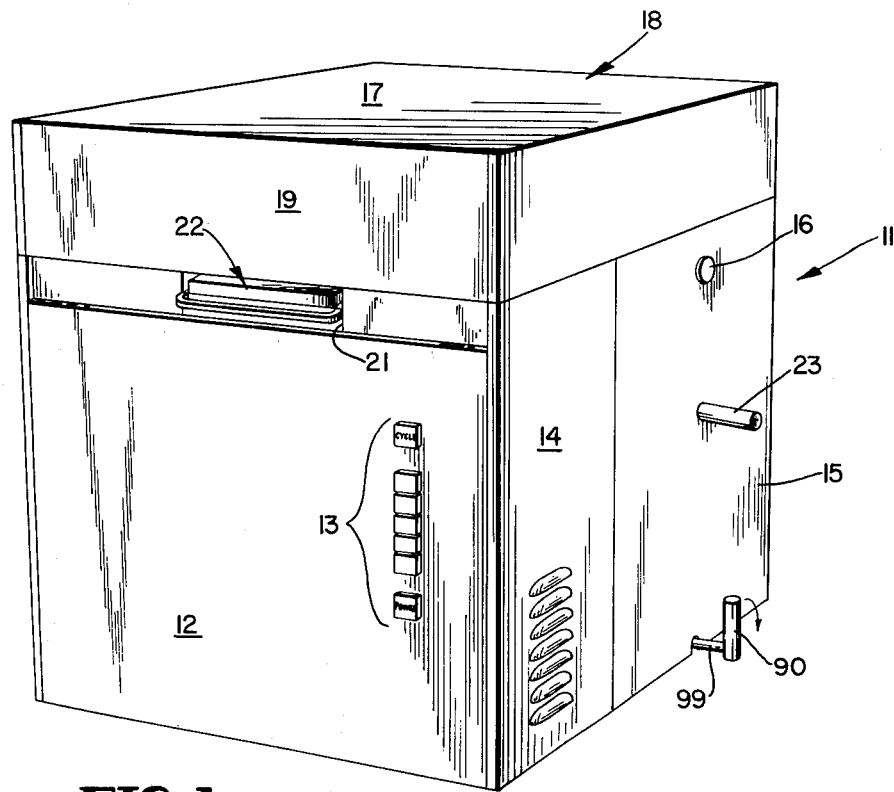
FIG. 1 is a generally perspective view showing a housing enclosing a preferred embodiment of the invention.

FIG. 1 shows a housing 11 wherein the system of the invention is enclosed and supported. Housing 11 comprises a front wall 12 through which extend the system control buttons 13, and a side wall 14 having a loading door 15 that is hinged near the bottom as will later be described and is normally held closed by a conventional push button operated latch indicated at 16.

The entire top of the housing which includes the top wall 17 and adjacent front, rear and side wall sections constitutes a top cover 18 that is hinged on the rear wall by means (not shown) to swing upwardly for access to the conduit and valve systems to be described.

As shown in FIG. 1 the front depending wall section 19 of the top cover closes the upper end of a front wall recess 21 through which is accessible a test tray assembly 22 later to be described in detail.

Figure 2:
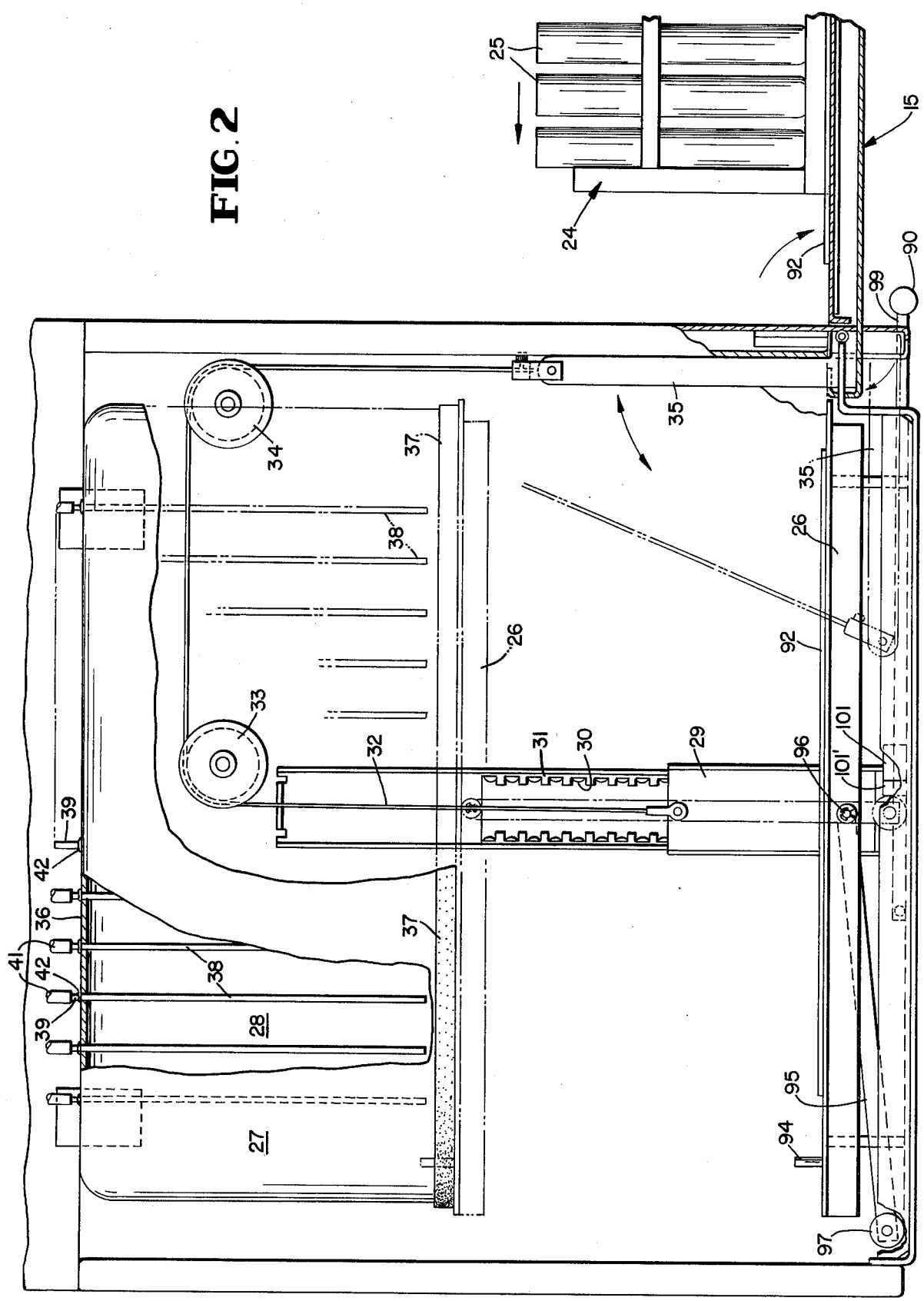
FIG. 2 is an enlarged side elevation, partly broken away and partly sectioned, showing the association of the loading door, elevator platform and pressure chamber of the assembly within the housing of FIG. 1.

FIG. 2 shows the side door 15 swung down to horizontal loading position. A leg 23 (FIG. 1) supports the door in this position. A rack 24 containing the required number of containers 25, which may be conventional test tubes, is shown mounted on the top surface of door 15, and during loading rack 24 is slidably pushed from the door onto the aligned level elevator platform 26 within the housing.

Platform 26 is mounted within the housing for vertical displacement between its lower full line loading and upper chain line unloading position of FIG. 2. In the upper position it acts as a pressure tight bottom closure for a downwardly open shell 27 defining a fluid pressure chamber 28.

Platform 26 has on opposite sides upstanding posts 29 that slide in vertical housing guides 31 (only one shown in FIG. 2). As shown in FIG. 2, each post 29 has ball bearings at 30 contacting the guides so that friction is greatly reduced and a very smooth lift operation is assured. Attached to the upper end of each post 29 is a flexible cable 32 that extends upwardly and over freely rotatable fixed axis rollers 33 and 34 and downwardly to be attached to the upper end of an arm 35 that comprises a rigid right angle extension of door 15. Arms 35 are spaced laterally of the doorway a distance that is wider than the platform. It follows therefore that, when the door 15 is rocked counterclockwise 90° to closed position in FIG. 2, arms 35 will similarly rock past the platform to the illustrated chain line position within the housing and pull down cables 32 to raise the elevator platform.

Shell 27 is fixedly mounted on a frame 30 removably mounted within the housing. Preferably shell 27 is an integral sheet metal unit having a top wall 36 and a resilient gasket 37 around the rim at its lower open end. A multiplicity of parallel stainless steel tubes 38 of the same length extend vertically downwardly within the shell to terminate in open ends near the open end of the shell. Each tube 38 extends through an opening in wall 36 (FIG. 2) to provide a short nipple formation 39 for receiving the end of flexible tubing indicated at 41, the purpose of which will be described later. An annulus of solder 42 surrounds each tube 38 where it extends through the wall 36, to thereby fix the tube to the shell and at the same time ensure that the wall opening is sealed pressure tight around the tube.

In practice adjacent stiff tubes 38 are equally spaced and the number, arrangement and spacing correspond exactly to the number, arrangement and spacing of the containers 25 on the rack 24. Thus if there are 96 containers on the rack in eight rows of twelve each, the tubes 38 are arranged in the same distribution, so that when the elevator platform 26 is automatically raised by closing door 15 each container 25 will raise to automatically receive an inserted tube 38.

Figure 4:
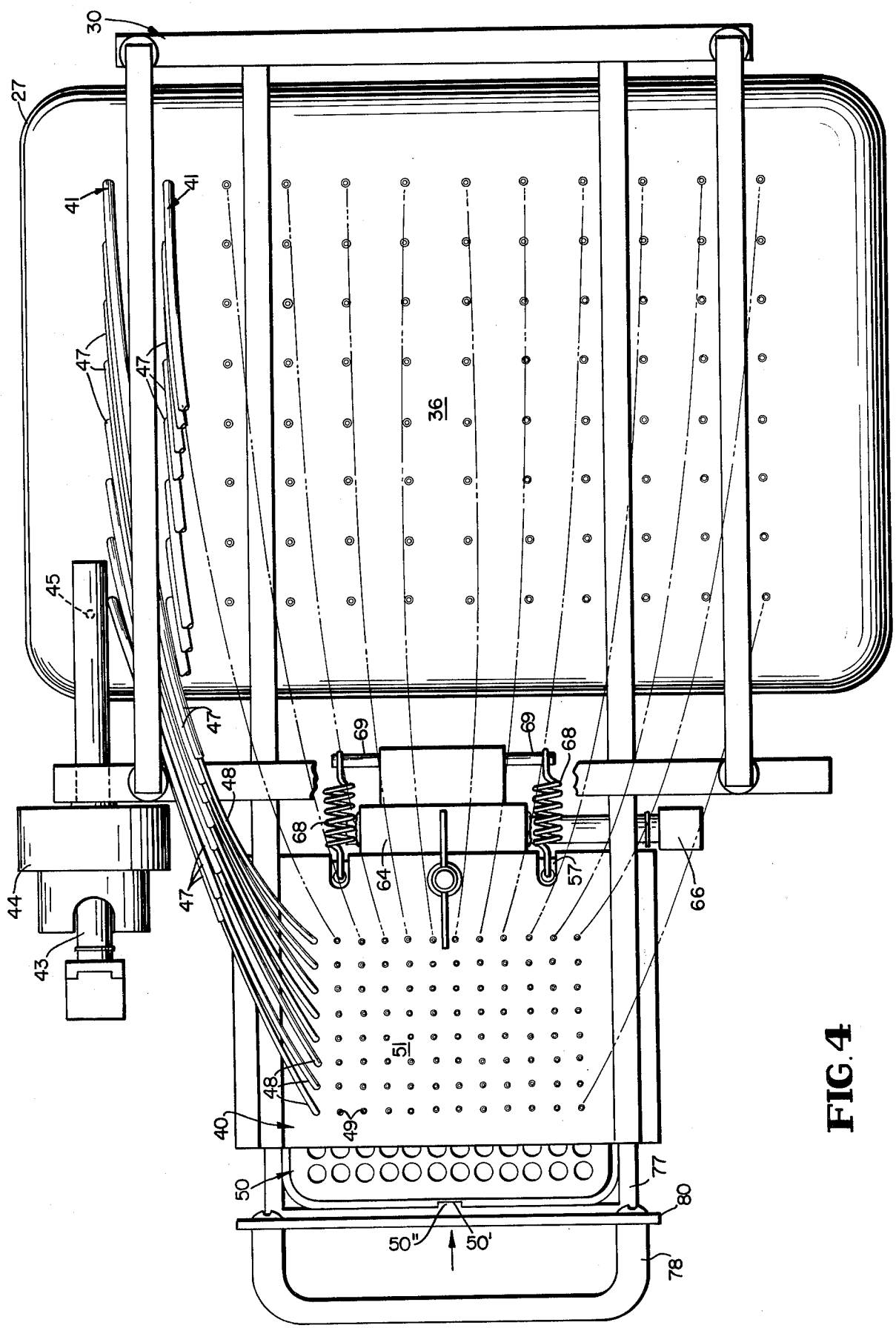
FIG. 4 is a top plan view showing the conduit system between the pressure chamber and the dispensing valve.

As shown in FIG. 4, fluid pressure in the form of pure air introduced into chamber 28 through a pipe connection 43 having a filter 44, the inlet to chamber 28 being indicated at 45.

Figures 3, 3A:
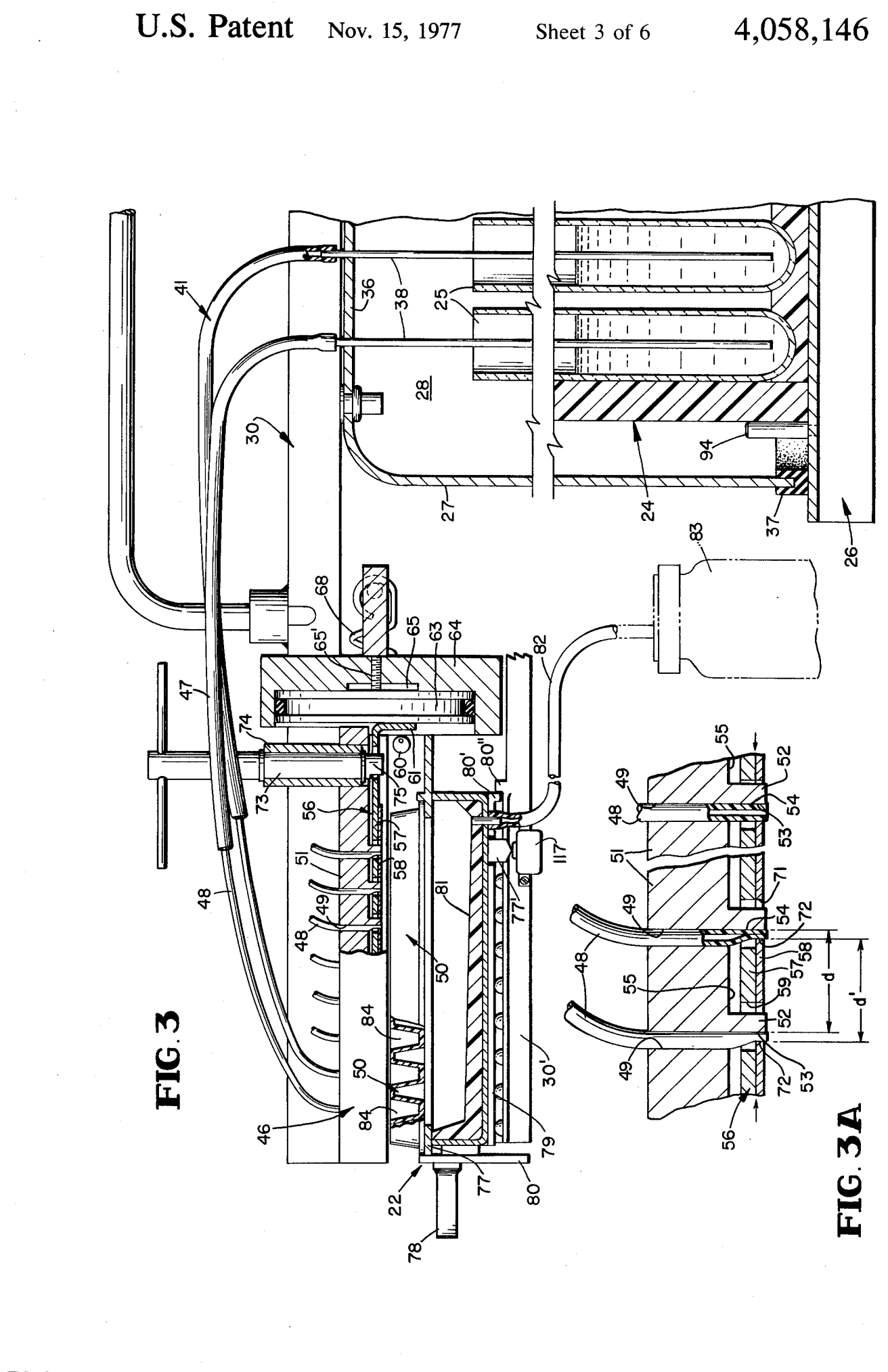

As shown in FIGS. 3 and 4, the conduit system comprising in this embodiment ninety-six lengths of flexible tubing 41 extends from the top of shell 27 to a dispensing valve assembly at 46. It is important to note that each length of tubing consists of a large diameter initial section 46 and a small diameter resilient wall discharge section 48. The small diameter sections are very accurately of the same length and uniform internal diameter. The large diameter sections are of the same internal diameter but they are of random length. In practice in a successfully operable system, the internal diameter of each small section is in the order of 0.032 inches while the internal diameter of the large diameter section is a minimum of twice that of the smaller diameter section. In some embodiments the small diameter sections may be of different length to discharge different amounts of liquid to the respective receptacles.

Preferably each tubing consists of silicone tubing which is inert chemically and biologically and has good resistance to temperature and wear by flexure.

The discharge ends of the tubing end sections 48 extend snugly through a series of holes 49 in a fixed horizontal valve plate 51 that is suitably secured on frame 30. As shown more clearly in FIG. 3A, a plurality of transverse depending ribs 52 are formed integral with the bottom of plate 51. Since there are ninety-six holes 29 arranged in eight transversely extending rows of twelve holes each, there are eight transverse ribs 52 of the same size. Ribs 52 are accurately formed with flat side faces 53 that are parallel to each other with adjacent faces very accurately equally spaced. Each face 53 lies in a plane substantially tangent to its associated row of circular holes 29 so that, as indicated in FIG. 3A, the terminal 54 of each tubing 48 lies in a substantial contact on one side with a rib face 53. This is shown more clearly of FIG. 3A which illustrates at the right the valve open condition of each dispensing tubing, and at the left side the valve closed condition of each tubing.

In practice it has been found important that the spacing between adjacent parallel rib surfaces 53, indicated at $d$ in FIG. 3A, be accurate within ± 0.001 inches.

Holes 49, as viewed from above in FIG. 4, are the same in number and arranged in the same relative location as tubes 38, and their location and spacing is exactly that of the wells in the test tray 50 to which liquid from the containers is to be transferred.

Ribs 52 define a series of transverse recesses 55 on the bottom of the fixed valve plate 51. A reciprocable valve plate unit 56 consisting of a rigid plate 57 to which is secured as by brazing or welding a relatively thin metal pinch plate 58 is mounted on the bottom of fixed valve plate 51. Plate 57 is formed with transverse apertures 59 that are wide enough to clear ribs 52 so that valve plate 56 may be physically disposed within recesses 55 for operative reciprocation in a plane as close as possible to the ends of tubing 48 and have sufficient clearance with respect to the ribs to enable it to reciprocate adequately in operation.

Figure 6:
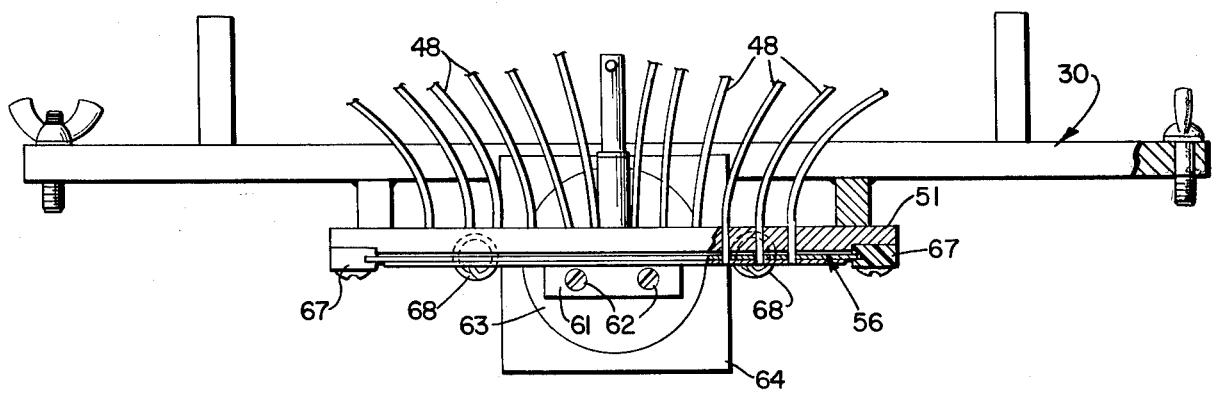
FIG. 6 is an end view partly broken away and sectioned showing the dispensing valve assembly in further detail.

At one end plate 57 is formed with a right angle flange 61 secured as by screws 62 to a piston 63 reciprocable in a cylinder 64 mounted on frame 30. A chamber 65 within cylinder 64 is supplied with fluid under pressure through a pneumatic fitting 66. The side edges of plate 57 are slidably supported in platic coated smooth guides 67 (FIG. 6) fixed on plate 51.

At its rear end plate 57 is connected by parallel laterally spaced coil tension springs 68 to posts 69 rigid with valve plate 51, so that the valve plate unit 56 is normally spring biased to the right in FIG. 3 to the valve closed position also shown in at the left side of FIG. 3A to pinch the ends of tubing sections 48 flat and tight against rib faces 53.

Figure 5:
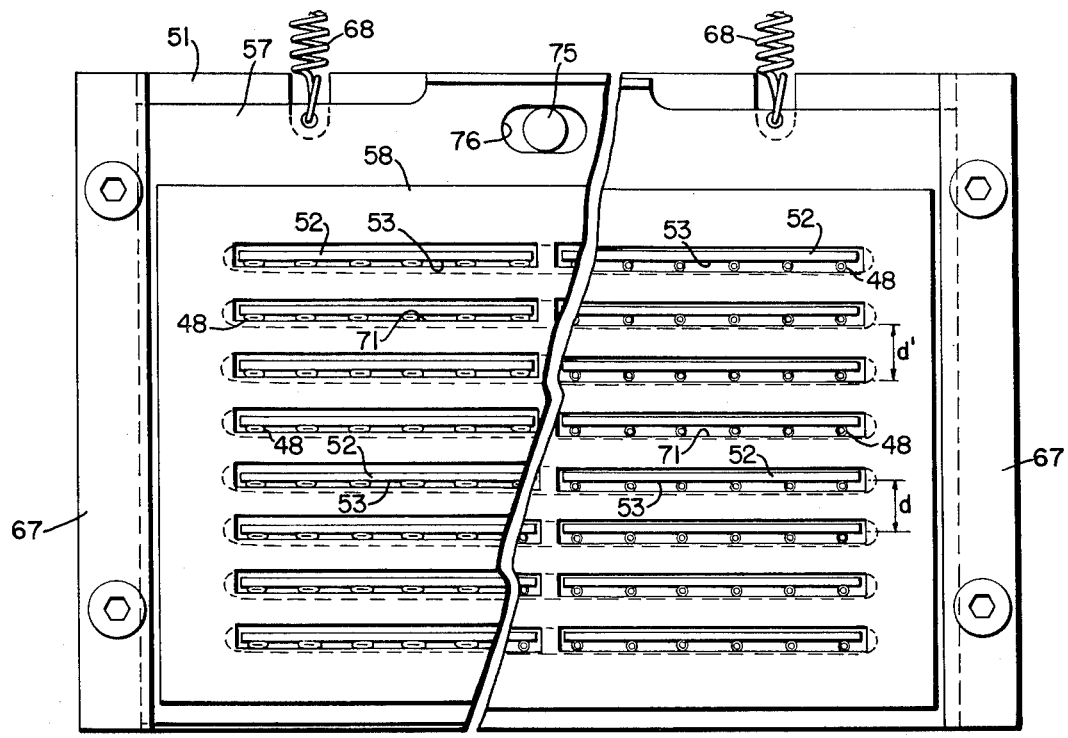
FIG. 5 is a bottom plan view of the dispensing valve assembly, broken to show the two valve positions.

Referring to FIGS. 3A and 5, it will be noted that the thin plate 58 is formed with apertures 71 that overlap the apertures in plate 57 along one side, so that when fluid pressure is applied to cylinder 64 to displace valve plate unit 56 against the action of springs 68 only a relatively short area of terminal 54 at substantially the tip of each resilient walled tubing 48 is clamped flat due to the fact that plate 58 is relatively thin and located on the bottom of plate 57. In practice plate 58 may be only about 0.005 to 0.010 inches in thickness. The tubing contacting edges 72 along apertures 71 are parallel and accurated spaced apart a distance $d'$ with the same tolerances as the spacing of rib faces 53, and it is the foregoing construction of valve plate unit 56 that permits this accuracy. The apertures in thin plate 58 may be formed by a photoetching operation with greater accuracy in tubing contacting edge spacing than a thicker plate. Thus the foregoing structure of the valve plate 56 provides for more accurate valve closing in that it limits the amount of tubing that has to be pinched to obtain valve closure, it reduces the force necessary to close the tubing, and it minimizes the time that the tubing takes to spring open when the fluid pressure is applied to the piston and displaces the valve plate.

By making the valve with the high degree of accuracy above detailed it is operable to obtain exactly similar opening and closing conditions in each of the 96 ends of tubing 48. Since the resilient wall tubing 48 is pinched at the discharge terminals the necessity for special nozzles is entirely eliminated and downstream turbulence usually encountered in known pinch valves is avoided.

The degree of valve opening during each transfer operation may be varied by provision of an adjustably mounted eccentric stop 60 in the path of valve plate 56 shown in fully open position in FIG. 3. By turning stop 60 and stroke of the piston is selected to permit various partial opening of all of the tubing ends at once. A micrometer adjustment may be provided here suitably calibrated and marked with a scale. In one position this stop may serve as the fully open limit stop. The degree to which the tubing ends are squeezed may be controlled by an adjustable stop 65' limiting movement of the piston to the right in FIG. 3.

The movable valve plate unit 56 may be manually moved to valve open position. A stem 73 is rotatably mounted in a column 74 fixed to plate 51 and carries on its lower end an eccentric button 75 disposed in a non-circular slot 76 in plate 57. When stem 73 is rotated it displaces the unit 56 between the valve closed and valve open positions illustrated at the respective left and right sides in FIG. 5.

The test tray 50 of the test tray assembly 22 is immovably mounted on a slidable carrier 77 having a pull handle 78. Advantageously the bottom of the tray 50 and the top surface of the carrier are provided with keying formation such as the ribs and recesses on the door and rack so that the tray may assume only one position on the carrier and thereby present the wells in exactly the same arrangement as the supply containers.

Carrier 77 is pulled out fully to place the tray 50 thereon and when pushed in fully each well 84 of the test tray is located accurately below the end of a tubing section 48. In the embodiment being described, the carrier is slidably mounted by means of a ball bearing slide 79 on a fixed support 30' rigid with frame 30. Carrier 77 is formed with an upwardly facing recess 81 connected by a conduit 82 to a liquid collect reservoir 83 for carrying away liquid discharged from the tubing when the tubing is primed with no test tray 50 in place before beginning operation. Suitable stops 80' and 80" respectively on carrier 77 and support 30' engage to limit inward movement of carrier 77.

Referring to FIG. 7 it will be noted that container rack 24 is formed with offset longitudinal recesses 90 and 91 slidably fitting with parallel guide ribs 92 and 93 on the door, so that the rack may be placed on the door in only one position for properly orienting the containers 25 with respect to the wells in the test tray 50. These ribs are reproduced in alignment on platform 26, and when the rack is pushed onto the platform and along these ribs it eventually encounters stop 94 in FIG. 3, which ensures it proper operative position below the pressure chamber.

In order to ensure that the platform 26 fully seals pressure tight with shell 27, a toggle mechanism is provided operated by the external handle 90 shown in FIGS. 1 and 7-9.

When the platform 26 is in its lowermost position, with door 15 open as shown in FIG. 2, a link 95 pivoted at 96 on the bottom of the platform extends freely generally horizontally and has a roller assembly on its other end resting on the bottom wall 100 of the housing. As illustrated in FIG. 10, link 95 is bifurcated at its lower end which carries two spaced rollers 97 and 98.

Handle 90 is on the outer end of a rod 99 that extends through a suitable opening in the door 15 and is rotatably mounted in a stop block 101 on the bottom wall of the housing. When the door is open, the handle is in the rotated horizontal position of FIG. 7, so that a radial pin 102 on the inner end of rod 99 is also horizontal as shown in FIG. 8.

When the door 15 reaches its closed position of FIG. 8, link 95 is almost vertical and platform 26 is usually in initial contact with the seal 37 around the edge of the shell.

As platform 26 rises under the pull of cables 32 the lower end of link 95 rolls toward the door past the pin bearing end of rod 99 to the approximate position of FIG. 8. After the door is latched the operator grasps handle 90, and rotates it 90° to vertical position, thereby raising pin 102 to vertical position (FIG. 9), and then pulls rod 99 outwardly. By the time handle 90 reaches the full line position of FIG. 9 upright pin 102 has engaged a cross bar 103 bridging the roller mounting arms and has forced the lower end of link 95 toward the FIG. 9 position where it is vertical and exerts a strong upward force urging the platform into tight sealed engagement with the shell, as shown in FIG. 9. Also block 101' on rod 99 now comes in contact with stop block 101 so that the link cannot move past the vertical position and it remains wedged firmly in position, and platform 26 cannot be relowered until the handle 50 has been pushed in force block 101' against the block to releaase the lock.

Figure 11:
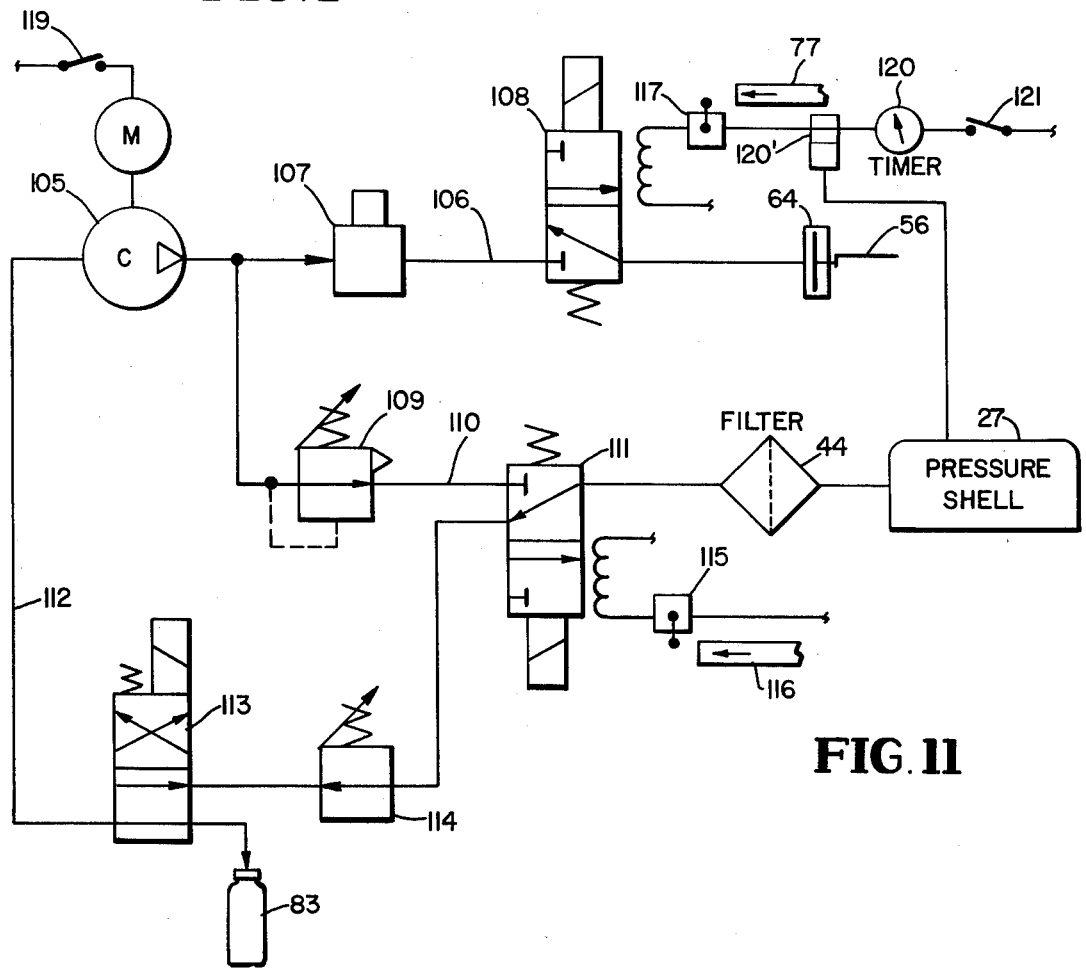
FIG. 11 is a schematic view showing the fluid pressure system.

FIG. 11 shows a pneumatic circuit enclosed within the housing. An electric motor drives an air compressor 105 that supplies air under pressure through a line 106 and a high pressure relief valve 107 and a three way normally closed spring return solenoid valve 108 to the cylinder for actuating the movable valve member 56.

Similarly the same source provides air under pressure in line 110 through a low pressure regulator 109 and a three way normally closed spring return solenoid valve 111 and air cleansing filter 44 to chamber 28 in the interior of shell 27.

The exhaust (vacuum side) of the compressor is connected through line 112 and a four way spring return solenoid valve 113 and a vacuum regulator 114 to a port in valve 111, for effecting purge of the system when desired. In one position valve 113 may connect line 112 to the reservoir 83.

A normally open switch 115 is disposed in the electric circuit powering solenoid 111 and means such as a pin 116 on rod 99 extending 90° with respect to pin 102 is provided to engage and close switch 115 when the 90° rotated rod has been pulled out to lock link 95 in the upright position of FIG. 9 after the chamber 28 is sealed at the bottom. As shown pin 116 follows a quide slot in a supporting collar on the housing wall. Thus pressure cannot be supplied to chamber 28 unless it is sealed pressure tight.

A normally open switch 117 is provided in the electrical circuit to solenoid 108 and this switch is closed only be engagement of a cam 77' on carrier 77 when the test tray carrier 77 has been pushed into its final operative position under the dispensing valve. This prevents the dispensing valve from being opened during testing except when the test tray carrier is fully pushed in, either for priming or for dispensing into a test tray.

The switches 115 and 117 may be otherwise suitably physically located as desired in the apparatus.

OPERATION

The compressor motor is energized to establish a source of fluid pressure and vacuum for system operation.

The stem 73 which is usually rotated to allow the tubing ends to open to prevent permanent deformation while the apparatus is idle is turned to release position, thus allowing the valve to close.

The containers filled with liquid or liquids to be dispensed are loaded on door 15 in rack 24 and the rack then pushed onto the elevator platform 26 which is raised to introduce the containers to receive the tubes 38 and provide the bottom of chamber 28. Then handle 90 is manipulated to complete the bottom pressure seal of chamber 28 and close interlock switch 115. When handle 90 has been pulled out fully it locks the toggle link 95 in position to maintain the pressure seal and this movement also closes switch 115 so that chamber 28 becomes automatically pressurized.

The conduit system at 41 may be primed by manually opening the dispensing valve and operating solenoid 111 to pressurize chamber 28 and thus fill conduits 41 with liquid up to the closed ends in the dispensing valve. The dispensing valve is now allowed to close with the conduits primed with liquid. The test tray 50 is placed on the carrier which is pushed in to close switch 117.

As shown in FIG. 4 tray 50 may be mounted only with proper orientation of its wells 84 with respect to containers 25 by provision of a lip recess 50' on one end only of the tray fitting with a corresponding projection 50| on the carrier plate.

The circuit to solenoid 108 is adjusted at timer 120 to set for a desired time cycle of operation wherein full air pressure will be supplied to cylinder 64 for a desired small dispensing time, and then the circuit to solenoid 108 is closed as by switch 121 in the control panel to pressurize cylinder 64 and open the dispensing valve for the desired discharge period. When the pressure in shell 27 rises to a predetermined amount it acts through a line 27' to close a normally open pressure switch 120' in the circuit of solenoid 108, thereby preventing system operation when the pressure is too low. During this dispensing period all of the tubing ends 48 are released at the same time to resiliently spring open and then reclosed under spring pressure.

The foregoing is accomplished by an electrical circuit (not otherwise shown) which is powered within the housing when the switch 119 is closed to energize the compressor motor.

The invention provides a relatively uncomplicated but extremely efficient test system which has a capacity of dispensing at least several hundred test trays an hour as compared to ten or twenty per hour in known apparatus for the purpose.

All parts are readily accessible, by opening door 15 and cover 18 and by removing front wall 12. When the cover 18 is open the frame 30 carrying the shell 27, the dispensing valve assembly and the conduits 41 all in operative interconnection may be lifted as a unit out of the housing for inspection and cleaning and repair if necessary.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of transferring identical small quantities of liquid from each of a multiplicity of individual supply containers arranged in predetermined relative locations to a corresponding multiplicity of closely spaced receptacles arranged in the same relative locations, with random spacing between the various associated pairs of receptacles and relatively located containers, which comprises the steps of establishing separate continuous passage direct fluid communications between each container and its associated receptacle, and simultaneously forcing liquid from each container into its associated receptacle for a predetermined time while relatively controlling the flow in each passage so that during said predetermined time the same measured amount of liquid is dispensed from each passage into each receptacle.

2. Apparatus for transferring identical small quantities of liquid from each of a multiplicity of individual supply containers arranged in predetermined relative locations to a corresponding multiplicity of closely spaced receptacles arranged in the same relative locations, with random spacing between the various associated pairs of receptacles and relatively located containers, which comprises means for establishing separate continuous passage direct fluid communication between each container and its associated receptacle, and means for simultaneously forcing liquid under pressure from each container into its associated receptacle for a predetermined time while relatively controlling the flow in each passage so that during said predetermined time the same measured amount of liquid is dispensed from each passage into each receptacle.

3. In the apparatus defined in claim 2, said passage means comprising individual conduits between each container and receptacle with each conduit terminating in a reduced diameter flow control section of the same length and flow passage cross section with its discharge end above the associated receptacle, and valve means operable upon said flow control sections to cyclically open and close all of said conduits to liquid flow at the same time.

4. In the apparatus defined in claim 3, said flow control sections being uniform diameter resilient tubing, and said valve means being operable to pinch and release said tubing substantially at said discharge ends.

5. A liquid transfer system comprising means defining a fluid pressure chamber, means for mounting a multiplicity to open top containers in said chamber each adapted to contain a supply of liquid to be transferred, means providing a corresponding multiplicity of passage defining elements within said chamber, each element being adapted to extend within an individual container and each being open at its upper end through the top of said chamber, a corresponding multiplicity of conduits each having one end connected to a passage defining element, valve means into which the other ends of said conduits extend, means in said valve means for normally holding said other ends of said conduits closed to liquid flow, means providing a multiplicity of closely spaced receptacles at said valve means, there being a receptacle aligned with the other end of each conduit, means for pressurizing said chamber to force liquid out of each container into and through its associated conduit, and means for actuating said valve means for simultaneously opening all of said conduit other ends for a predetermined time to allow discharge of liquid into all of the associated receptacles for said predetermined time.

6. The system defined in claim 5, including a support on which said pressure chamber is mounted, said chamber being open at its lower end, said container mounting means comprising a lift platform below said chamber adapted to receive a rack or the like carrying open top containers of said liquid and means for raising said platform into bottom sealing relation with said chamber with a passage defining element projecting within each container.

7. A liquid transfer system comprising means defining a fluid pressure chamber, means for mounting a multiplicity of open top containers in said chamber each adapted to contain a supply of liquid to be transferred, means providing a corresponding multiplicity of passage defining elements within said chamber, each element being adapted to extend within an individual container and each being open at its upper end through the top of said chamber, a corresponding multiplicity of conduits each having one end connected to a passage, valve means into which the other ends of said conduits extend, means in said valve means for normally holding said other ends of said conduits closed to liquid flow, means for pressurizing said chamber to force liquid out of each container into and through its associated conduit, means for actuating said valve means for simultaneously opening all of said conduit other ends for a predetermined time to allow discharge of liquid into all of the associated receptacles for said predetermined time, a support on which said pressure chamber is mounted, said chamber being open at its lower end, said container mounting means comprising a lift platform below said chamber adapted to receive a tray or the like carrying open top containers of said liquid, means for raising said platform into bottom sealing relation with said chamber with a passage defining element projecting within each container, said support comprises a housing having a side opening closed by a movable door, means whereby said door in open position provides a generally horizontal loading platform for said rack of containers in substantial alignment with the lift platform, and means interconnecting said door and platform whereby when said door is closed after the rack is moved onto the platform, said platform is automatically lifted to the bottom of said chamber.

8. The system defined in claim 7, wherein said door in loading position has index formations that key with index formations on the rack so that said rack may be loaded and moved onto said platform in only one oriented disposition.

9. The system defined in claim 7, wherein positive means is provided operable at the end of the lift operation for forcing and maintaining said platform in pressure tight sealed contact with said chamber.

10. The system defined in claim 9, wherein said positive means comprises toggle linkage between the platform and support and a manually operable member extending through the door for effecting movement of the linkage to effect final lift movement of the platform to sealing engagement with the chamber.

11. The system defined in claim 10, wherein means including an electrically controlled solenoid valve provides fluid pressure to said chamber and switch means in the energizing circuit of said solenoid is provided on the support located to be actuated by said member to open said solenoid valve when the platform is in sealed contact with said chamber.

12. In apparatus for simultaneously transferring small metered amounts of liquid from each of a multiplicity of containers to a corresponding multiplicity of closely adjacent receptacles where some of the receptacles are disposed at different distances from the associated containers, means providing individual continuous direct passage between each container and its associated receptacle, pinch valve means operable for closing and periodically opening the passages disposed adjacent the discharge ends of said passages, all of said passages comprising at their discharge ends resilient terminal sections that terminate in said pinch valve means and are of such predetermined length and internal flow passage cross sectional area as to provide substantially equal resistance to liquid flow therethrough and discharge of substantially equal amounts of liquid from each passage during valve open periods, and there being passage sections of appreciably larger internal flow passage cross sectional area extending from said terminal sections to the respective containers.

13. In the apparatus defined in claim 12, said terminal sections each having a cross sectional area not more than one-half the cross sectional area of the remainder of the passage.

14. In the apparatus defined in claim 12, each terminal section being a length of relatively small diameter resilient walled tubing of essentially the same accurately predetermined effective length and flow characteristics, and said valve means comprising means for normally pinching the tubing ends closed and for periodically allowing said tubing ends to open for a time sufficient to discharge a predetermined small amount of liquid into each receptacle.

15. In apparatus for simultaneously transferring metered amounts of liquid from each of a number of containers to a corresponding number of receptacles where some of the receptacles are disposed at different distances from the associated containers, and wherein said receptacles are open top cells in a single test tray means providing individual passages between each container and its associated receptacle, valve means operable for closing and opening the passages disposed adjacent the discharge ends of said conduits, all of said passages comprising at their discharge ends terminal conduit sections of the same length and internal flow passage cross sectional area regardless of the overall length of the passage and sections of appreciably larger internal flow passage cross sectional area extending from the terminal sections to the containers, mounting means for said tray movable between a locating position and a receptacle fill position below said valve means with each tubing and located above a different cell, and means whereby said valve means is inoperable to open the conduit ends unless the tray is moved into said fill position.

16. In the apparatus defined in claim 14, said valve means comprising a movable member spring biased to move in one direction and connected to a fluid pressure responsive operator and disposed adjacent the tubing ends, and means whereby said operator is periodically actuated to effect simultaneously opening of all of said tubing ends for a predetermined time.

17. In the apparatus defined in claim 2, wherein said containers are mounted on a detachable common support member that may be loaded apart from the apparatus and inserted into the apparatus for liquid transfer operations, and said receptacles are wells in a tray-like member that is detachably mounted in the apparatus so as to be removed after a liquid transfer operation, each of said members being provided with formations that interfit only with corresponding indexing formations in said apparatus so that said members may be operatively placed in the apparatus only in such relative position as to ensure during operation transfer of liquid from each container to an identified corresponding receptacle.

18. In the apparatus defined in claim 2, said last named means comprising individual conduits between each container and receptacle with each conduit terminating in a reduced diameter flow control section of predetermined length and flow passage cross section with its discharge end above the associated receptacle, each flow control section being of such size relative to the others as to provide discharge of accurately predetermined relative amounts of liquid from each conduit, and said valve means being operable upon said flow control sections to cyclically open and close all of said conduits to liquid flow at the same time.

19. In the system defined in claim 5, means for preventing operation when the pressure in said chamber is below a predetermined amount.

20. In the apparatus defined in claim 2, said passage means comprising individual uninterrupted tubing members extending from each container to its associated receptacle, and the discharge ends of all of said tubing members being constructed and arranged to offer substantially identical resistance to fluid flow therethrough so that they thereby discharge the same amount of fluid during said predetermined time.

21. In the apparatus defined in claim 20, each tubing member comprising a substantially integral length of resilient tubing, and there being cyclically operable pinch valve means effectively connected to the discharge ends of all of said lengths of tubing.

22. Apparatus for transferring identical small quantities of liquid from each of a multiplicity of individual supply containers arranged in predetermined relative locations to a corresponding multiplicity of small capacity open receptacles arranged in the same relative locations, with random spacing between the various associated pairs of receptacles and relatively located containers, which comprises individual lengths of tubing of random length extending to establish direct separate fluid communication between each container and its associated receptacle and terminating at the receptacle in a resilient discharge section and means including pinch valve means within which said resilient discharge ends terminate for simultaneously delivering liquid under pressure from each container into its associated receptacle for a predetermined time while relatively controlling the flow in each tubing so that during said predetermined time the same amount of liquid is discharged from each tubing into its associated receptacle.

23. In apparatus for simultaneously transferring metered small amounts of liquid directly from a number of individual supply containers to a corresponding number of receptacles in the form of open top wells in a test tray wherein each of said wells has an identifiable positional relationship to a respective associated container and some of the wells are disposed at different respective distances from their associated containers, means providing individual lengths of resilient tubing extending from each container, means disposing the discharge end of each tubing length above its associated well, and cyclically operable pinch valve means receiving the discharge ends of said tubing lengths for closing and periodically opening all of said tubing lengths for simultaneous accurate discharge of predetermined small amounts of liquid into said wells during valve open periods.

* * * * *

UNITED STATES PATENT OFFICE
CERTIFICATE OF CORRECTION

Patent No. 4,058,146                    Dated   November 15, 1977

Inventor(s)   Paul S. Citrin

It is certified that error appears in the above-identified patent and that said Letters Patent are hereby corrected as shown below:

Column 3, line 35 change "46" to --47-- .

Column 5, line 49 change "it" to --its-- .

Column 7, line 25 change "50/" to --50"--.

Column 8, line 45, Claim 5 change "to" to --of--.

Signed and Sealed this

Sixteenth Day of May 1978

[SEAL]

Attest:

RUTH C. MASON  
Attesting Officer

LUTRELLE F. PARKER  
Acting Commissioner of Patents and Trademarks